(12) United States Patent
Frings et al.

(10) Patent No.: US 11,705,229 B2
(45) Date of Patent: Jul. 18, 2023

(54) METHOD AND DEVICE FOR EXCHANGING INFORMATION REGARDING THE CLINICAL IMPLICATIONS OF GENOMIC VARIATIONS

(71) Applicant: Siemens Healthcare GmbH, Erlangen (DE)

(72) Inventors: Oliver Frings, Erlangen (DE); Maximilian Wuerstle, Baiersdorf (DE); Eugen Kubala, Erlangen (DE); Dominik Neumann, Erlangen (DE); Maximilian Weiss, Erlangen (DE); Carsten Dietrich, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 441 days.

(21) Appl. No.: 17/015,348

(22) Filed: Sep. 9, 2020

(65) Prior Publication Data
US 2021/0082546 A1 Mar. 18, 2021

(30) Foreign Application Priority Data
Sep. 16, 2019 (EP) ..................................... 19197515

(51) Int. Cl.
*G06F 21/31* (2013.01)
*G16H 10/60* (2018.01)
(Continued)

(52) U.S. Cl.
CPC .............. *G16H 10/60* (2018.01); *G06F 21/31* (2013.01); *G06F 21/6227* (2013.01);
(Continued)

(58) Field of Classification Search
CPC ...... G06F 21/6227; G06F 21/31; G16H 70/20
See application file for complete search history.

(56) References Cited

U.S. PATENT DOCUMENTS 7,461,006 B2 * 12/2008 Gogolak ................ G16B 20/20
435/5
11,074,262 B2 * 7/2021 Eifert .................... G06V 30/416
(Continued)

OTHER PUBLICATIONS

Huang, Linda et al. "The cancer precision medicine knowledge base for structured clinical-grade mutations and interpretations" Journal of the American Medical Informatics Association, vol. 24. No. 3, pp. 513-519, 2017 // doi: 10.1093/jamia/ocw148.
(Continued)

*Primary Examiner* — Eliyah S. Harper
(74) *Attorney, Agent, or Firm* — Harness, Dickey & Pierce, P.L.C.

(57) ABSTRACT

A method and a device are for exchanging information regarding the clinical implications genomic variations. In an embodiment, the method includes receiving login-data of a user; evaluating the login-data received; establishing an encrypted data connection to the user after the evaluating indicates a positive evaluation of the login-data; saving, upon receiving a dataset in a context of a genomic variation, the dataset received in a memory, context-related with the genomic variation; and evaluating, upon a user request being received and connected with a search query for the genomic variation, a set of datasets from the memory, the datasets being context-related with the genomic variation and the set including the datasets that the user is authorized to receive, and sending the set of datasets to the user.

24 Claims, 5 Drawing Sheets

(51) Int. Cl.
*G16H 70/20* (2018.01)
*G16H 80/00* (2018.01)
*G16B 50/30* (2019.01)
*G16B 20/00* (2019.01)
*G06F 21/62* (2013.01)

(52) U.S. Cl.
CPC .............. *G16B 20/00* (2019.02); *G16B 50/30* (2019.02); *G16H 70/20* (2018.01); *G16H 80/00* (2018.01); *G06F 2221/2141* (2013.01)

(56) References Cited

U.S. PATENT DOCUMENTS

| | | | | |
|---|---|---|---|---|
| 11,120,369 | B2* | 9/2021 | Barrett | G16B 20/20 |
| 11,183,268 | B2* | 11/2021 | Glode | G06F 3/0482 |
| 2013/0013603 | A1* | 1/2013 | Parker | G06F 16/353 |
| | | | | 707/E17.046 |
| 2013/0091126 | A1* | 4/2013 | Krishnaswami | G06F 16/9038 |
| | | | | 707/722 |
| 2013/0144887 | A1* | 6/2013 | Chen | G16C 20/70 |
| | | | | 707/748 |
| 2014/0280086 | A1* | 9/2014 | Bouadjenek | G06F 16/2228 |
| | | | | 707/723 |
| 2015/0088888 | A1* | 3/2015 | Brennan | G06F 16/24578 |
| | | | | 707/737 |
| 2016/0048564 | A1* | 2/2016 | Bassett, Jr. | G16B 50/00 |
| | | | | 715/230 |
| 2016/0210426 | A1* | 7/2016 | Robinson | G06Q 10/10 |
| 2016/0232321 | A1* | 8/2016 | Silverman | G16H 50/50 |
| 2017/0225743 | A1* | 8/2017 | Hara | B62M 9/133 |
| 2018/0081859 | A1* | 3/2018 | Snider | G06F 40/44 |
| 2018/0137433 | A1* | 5/2018 | Devarakonda | G06N 5/022 |

OTHER PUBLICATIONS

Fiume, Marc "System for Interpretation of Personal Genomes" Doctoral Thesis, University of Toronto, 2015 // ISBN: 9781339359274; https://tspace.library.utoronto.ca/bitstream/1807/69278/3/Fiume_Marc_201506_PhD_thesis.pdf.

"Clinical Practice" amp.org, Clinical Practice Guidelines, https://www.amp.org/clinical-practice/practice-guidelines/ 2019.

Tan, Powell Patrick Cheng et al. "Interactive Exploration, Analysis, and Visualization of Complex Phenome-Genome Datasets with ASPIREdb" Human Mutation, vol. 37, No. 8, pp. 719-726, 2016 // https://doi.org/10.1002/humu.23011.

"CIViC" civicdb.org, Online data sharing platform, https://civicdb.org/home 2019.

Warner, Jeremy L. et al. "SMART Cancer Navigator: A Framework for Implementing ASCO Workshop Recommendations to Enable Precision Cancer Medicine" JCO Precision Oncology, vol. 2, 2018 // DOI: 10.1200/PO.17.00292.

(HGVS) "Sequence Variant Nomenclature" http://varnomen.hgvs.org/ 2019.

(ESCAT) "ESMO Scale for Clinical Actionability of molecular Targets" esmo.org; https://www.esmo.org/Policy/ESCAT 2019.

Extended European Search Report for European Application No. 19197515.0 dated Feb. 19, 2020.

* cited by examiner

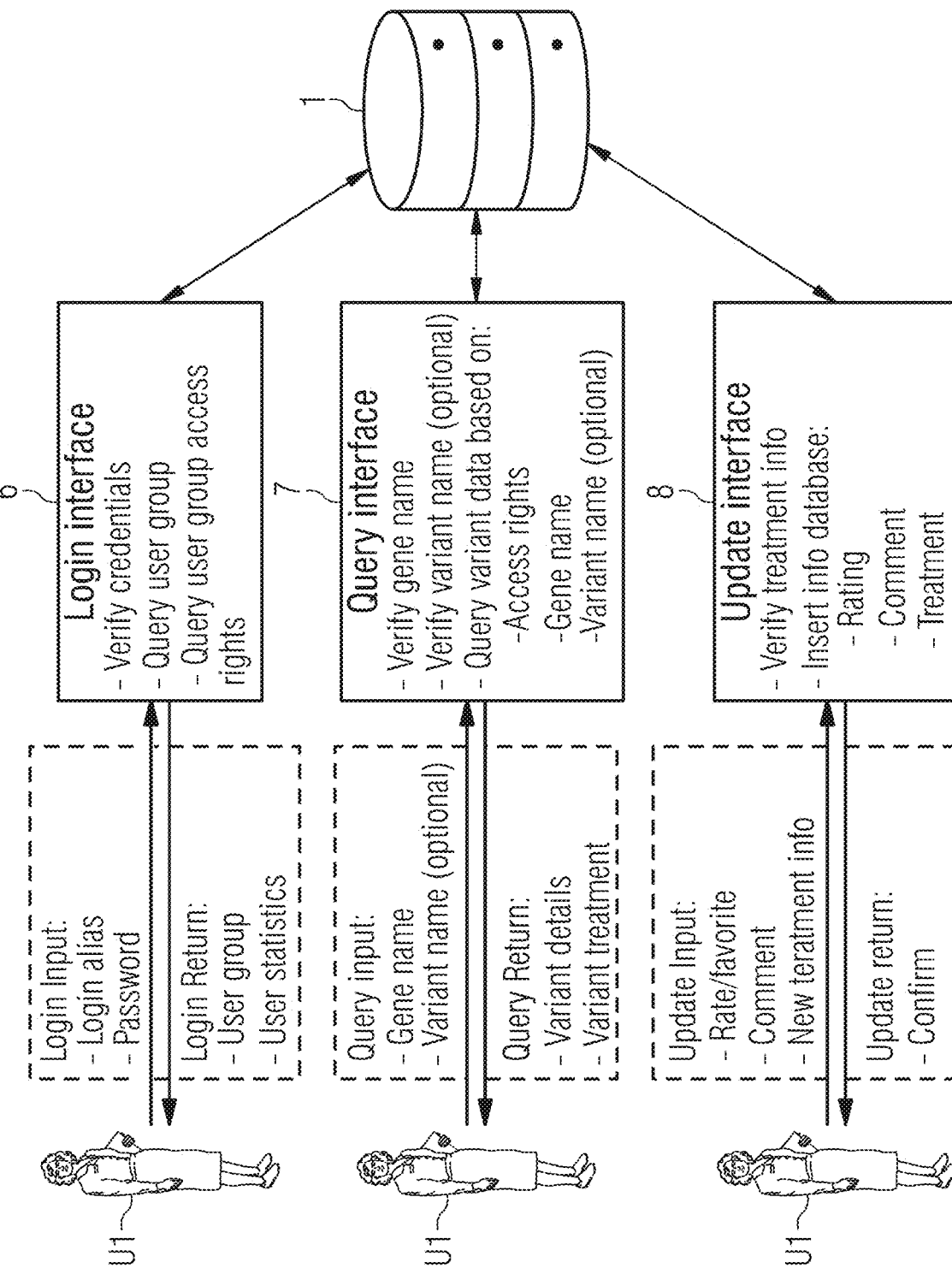

METHOD AND DEVICE FOR EXCHANGING INFORMATION REGARDING THE CLINICAL IMPLICATIONS OF GENOMIC VARIATIONS

PRIORITY STATEMENT

The present application hereby claims priority under 35 U.S.C. § 119 to European patent application number EP19197515.0 filed Sep. 16, 2019, the entire contents of which are hereby incorporated herein by reference.

FIELD

Embodiments of the invention generally relate to a method and a device for exchanging information regarding the clinical implications of genomic variations.

BACKGROUND

Clinical oncology is a rapidly evolving field and therefore clinical guidelines might not always represent the current clinical best practice or reflect the latest research findings.

For example, more and more cancer therapies are targeting specific molecular abnormalities in cancer cells, so called somatic variants. Targeted cancer therapies are usually only certified for a particular entity, since not enough evidence is available for other entities. Off-label prescription of anti-cancer drugs, e.g. in cancer patients with a specific somatic variant in an entity other than the entity that a drug was originally certified for, is common practice for patients with advanced cancer stage. Especially for patients that have received 2-3 rounds of unsuccessful treatment, it often represents the last viable option.

However, since it is often not clear which patients might benefit from a certain treatment and treatment response can also be influenced by other genetic changes present in a patient, it is difficult to find the right treatments for individual patients. In particular, for drugs targeting rare genetic variants the collection of clinical evidence is often challenging and time consuming.

Today, somatic variant annotations are typically exchanged between doctors within the same institution by using in-house customized database systems. Other possibilities include the use of email or other online data sharing platforms (e.g. Civic: civicdb.org) for the exchange between doctors and or scientists. Another option is the publication of case reports in scientific journals.

SUMMARY

At least one embodiment of the present invention improves upon the known systems, devices and methods to facilitate an improvement in exchanging medical information.

A method, according to at least one embodiment of the invention, serves for exchanging information regarding the clinical implications of genomic variations. The environment, where the method is used, is a common client-server system in a data-network, wherein the method is performed on the server and the users work with the clients connected with the server. A preferred architecture is a (especially cloud-based) database that is accessible by different authorized hospitals and persons. The method comprises:

receiving login-data of a user,
evaluating the login-data, and
establishing an encrypted data connection between the user and the device after a positive evaluation of the login data, e.g. over a data-network.

For at least one embodiment of the method it is important that the data connection is rendered such that: a) in the case of receiving a dataset in the context of a genomic variation, the received dataset is saved in the memory context-related with this genomic variation and b) in the case of a user request connected with a search query for a genomic variation, a set of datasets is evaluated from the memory, wherein the datasets are context-related with this genomic variation, and the set comprises those datasets that the user is authorized to receive. This set is sent to the user.

At least one embodiment of the invention is directed to a method for exchanging information regarding clinical implications of genomic variations, comprising:

receiving login-data of a user;
evaluating the login-data received;
establishing an encrypted data connection to the user after the evaluating indicates a positive evaluation of the login-data;
saving, upon receiving a dataset in a context of a genomic variation, the dataset received in a memory, context-related with the genomic variation; and
evaluating, upon a user request being connected with a search query for the genomic variation, a set of datasets from the memory, the datasets being context-related with the genomic variation and the set including the datasets that the user is authorized to receive, and sending the set of datasets to the user.

The device of at least one embodiment comprises a data-interface designed for the exchange of (digital) data over a network, a (data) memory designed for saving data pertaining to clinical implications of genomic variations and a computing unit designed for evaluating login-data of a user received over the data-interface,
establishing an encrypted data connection between the user and the device after a positive evaluation of the login data, wherein
a) in the case of receiving a dataset in the context of a genomic variation:
saving the received dataset in the memory context-related with this genomic variation and
b) in the case of a user request connected with a search query for a genomic variation:
evaluate a set of datasets from the memory, wherein the datasets are context-related with this genomic variation and the set comprises these datasets that the user is authorized to receive, and send this set of datasets to the user.

At least one embodiment of the invention is also directed to a computer program product with a computer program that is directly loadable into the memory of a device of a device, and which comprises program units to perform the steps of at least one embodiment of the inventive method when the program is executed by the device. In addition to the computer program, such a computer program product can also comprise further parts such as documentation and/or additional components, also hardware components such as a hardware key (dongle etc.) to facilitate access to the software.

At least one embodiment is directed to a computer readable medium such as a memory stick, a hard-disk or other transportable or permanently-installed carrier can serve to transport and/or to store the executable parts of the computer program product so that these can be read from a processor unit of a device. A processor unit can comprise one or more microprocessors or their equivalents.

At least one embodiment is directed to a device for exchanging information regarding clinical implications of genomic variations, comprising:

a data-interface designed for exchange of data over a network;

a memory designed for saving data pertaining to clinical implications of genomic variations; and a computing unit designed for evaluating login-data of a user received via the data-interface;

establishing an encrypted data connection between the user and the device after the evaluating indicates a positive evaluation of the login data;

saving, upon receiving a dataset in a context of a genomic variation, the dataset received in the memory, context-related with the genomic variation; and evaluating, upon a user request being received and connected with a search query for the genomic variation, a set of datasets from the memory, the datasets being context-related with the genomic variation and the set including the datasets that the user is authorized to receive, and sending the set of datasets to the user.

At least one embodiment is directed to a non-transitory computer program product storing a computer program, directly loadable into a server and including program elements for performing at least one embodiment of the method when the computer program is executed by the server.

At least one embodiment is directed to a non-transitory computer-readable medium storing program elements, readable and executable by a computer unit, to perform at least one embodiment of the method of when the program elements are executed by the computer unit.

BRIEF DESCRIPTION OF THE DRAWINGS

Other objects and features of the present invention will become apparent from the following detailed descriptions of example embodiments considered in conjunction with the accompanying drawings. It is to be understood, however, that the drawings are designed solely for the purposes of illustration and not as a definition of the limits of the invention.

FIG. 4 shows the inner architecture of a device according to an embodiment of the invention.

In the diagrams, like numbers refer to like objects throughout. Objects in the diagrams are not necessarily drawn to scale.

DETAILED DESCRIPTION OF THE EXAMPLE EMBODIMENTS

Figure 1:
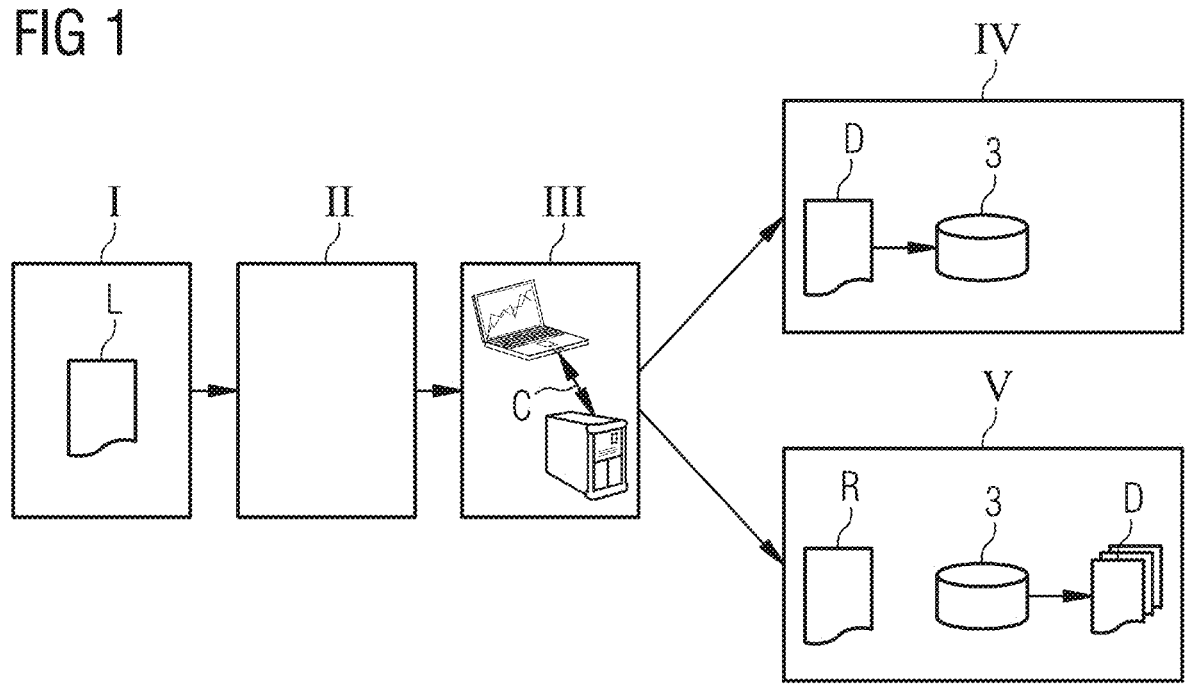
FIG. 1 shows a diagram of the process flow of a preferred method according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method, according to at least one embodiment of the invention, serves for exchanging information regarding the clinical implications of genomic variations. The environment, where the method is used, is a common client-server system in a data-network, wherein the method is performed on the server and the users work with the clients connected with the server. A preferred architecture is a (especially cloud-based) database that is accessible by different authorized hospitals and persons. The method comprises:

receiving login-data of a user,
evaluating the login-data, and
establishing an encrypted data connection between the user and the device after a positive evaluation of the login data, e.g. over a data-network.

For at least one embodiment of the method it is important that the data connection is rendered such that: a) in the case of receiving a dataset in the context of a genomic variation, the received dataset is saved in the memory context-related with this genomic variation and b) in the case of a user request connected with a search query for a genomic variation, a set of datasets is evaluated from the memory, wherein the datasets are context-related with this genomic variation, and the set comprises those datasets that the user is authorized to receive. This set is sent to the user.

It should be noted that the "genomic variation" (i.e. a genetic variant) can be identified by a gene and a variation of this gene. A user request can comprise an identification of a gene (to receive information of possible variants) or an identification of a gene and a variation of this gene.

Regarding the step of receiving login-data of a user, this is well known in the state of the art. Typically, the user enters his username together with his password. In praxis, the user inputs the login data at a client that sends the login data to the server. Surely, other known login routines may be used, alternatively. The expressions "user" and "client" can be used synonymously regarding the invention, since the user uses a client (a computer terminal) to connect to the server and to enter input data and to receive output data.

Regarding the step of evaluating the login-data, the server evaluates whether the user is authorized to log in or not, i.e. whether the entered password matches the correct password for the username.

Regarding the step of establishing an encrypted data connection (e.g. a VPN connection) to the user after a positive evaluation of the login data, it is clear that technically, the server establishes this encrypted data connection with the client of the user. This step is well known.

In the course of the encrypted communication (i.e. between the server and said client), data can be received from the user (from his client) that should be shared with others or data can be sent to other users in the act of sharing. Each dataset should be connected with a genomic variation and comprise information about members of the group treatments, examinations, discoveries, pictures, quantities, questions and other topics related with medical measurements or interventions. Another possible expression for a dataset is "annotation" or "entry".

A dataset could comprise an information about users that are authorized to use this dataset, however, this is not always necessary, since the missing of such information can be interpreted in that all users may use this dataset.

In the case when such dataset is received, this dataset is saved in a (data)memory, wherein the dataset must be saved context-related with this genomic variation. "Context-related" means here that it must be possible that the dataset is found during a search connected with this genomic variation. This can e.g. be achieved by saving the dataset linked to the genomic variation (e.g. a string characterizing this variation) or in a folder pertaining to this genomic variation. However, every database saves data in a context-related way. The server (hardware) can comprise a database (software) with a database management system designed for the method of at least one embodiment of the invention.

For context related saving as well as for a search query, the genomic variation must be identified (and correctly indicated). A genomic variation can be identified by the following preferred methods:

With an unique gene ID, e.g. with a Entrez Gene ID,
With an unique transcript ID or specific genomic regions incl. reference genome (for genomic rearrangements and copy number variations),
With a variant definition according to Sequence Variant Nomenclature (HGVS http://varnomen.hgvs.org/).

Further, important information can be provided with an assignation of an evidence class describing the clinical actionability, e.g. according to AMP (https://www.amp.org/clinical-practice/practice-guidelines/) or ESCAT (https://www.esmo.org/Policy/ESCAT). The evidence class (AMP/ESCAT) is advantageous as a complementing information. Additionally, it is preferred that there is the possibility to add free text describing the variant and how it should be treated in a clinical context (e.g. functional and phenotypically implications, drug sensitivity or resistances, prognostic implications, pharmacogenetics, and patient follow-up data incl. treatment response). A free text field as input option allows a user to add comments.

In the case of a user request connected with a search query for a genomic variation datasets stored in the memory should be sent to the user. However, in the case that there is a dataset that is marked to be used only by a special group of users, a user not in this group should not get this dataset. Thus, after a user logged in (see above) and enters a search query relating to a genomic variation, there is evaluated a set of datasets connected with this genomic variation. This set of datasets comprises datasets of the memory that are context-related with this genomic variation, but may not comprise all related datasets. In the course of this evaluation it is also evaluated which datasets the user is authorized to receive. Datasets the user is authorized to receive will be included in this set, datasets the user is not authorized to receive will not be included in the set. This set is then sent to the user (i.e. the client of the user).

With this method of at least one embodiment, a system can be realized that allows medical doctors and researchers to exchange information regarding the clinical implications of genomic variations, such as somatic variants, germline variants, genomic rearrangements, and copy number variations, in a fast and standardized manner. This is of great value for patients and the healthcare system in general. Improving patient outcome by bringing knowledge from different clinics to the right patients not only avoids unnecessary treatments, but also helps to reduce costs.

A device according to at least one embodiment of the invention is able to exchange information regarding the clinical implications of genomic variations. Instead of the designation "device", the designation "server" could be used, since the device acts as server in a network. Preferably, also the designation "database" can be used, since the device acts as a database.

The device of at least one embodiment comprises a data-interface designed for the exchange of (digital) data over a network, a (data) memory designed for saving data pertaining to clinical implications of genomic variations and a computing unit designed for evaluating login-data of a user received over the data-interface,
establishing an encrypted data connection between the user and the device after a positive evaluation of the login data, wherein
a) in the case of receiving a dataset in the context of a genomic variation:
saving the received dataset in the memory context-related with this genomic variation and
b) in the case of a user request connected with a search query for a genomic variation:
evaluate a set of datasets from the memory, wherein the datasets are context-related with this genomic variation and the set comprises these datasets that the user is authorized to receive, and send this set of datasets to the user.

The device serves as server in a data network, where users may access via clients to the information stored in the memory. The server preferably performs the method according to at least one embodiment of the invention to allow sharing of the datasets.

Some units or modules of the device mentioned above can be completely or partially realized as software modules running on a processor of a device. A realization largely in the form of software modules can have the advantage that applications already installed on an existing system can be updated, with relatively little effort, to install and run these units of the present application.

At least one embodiment of the invention is also directed to a computer program product with a computer program that is directly loadable into the memory of a device of a device, and which comprises program units to perform the steps of at least one embodiment of the inventive method when the program is executed by the device. In addition to the computer program, such a computer program product can also comprise further parts such as documentation and/or additional components, also hardware components such as a hardware key (dongle etc.) to facilitate access to the software.

At least one embodiment is directed to a computer readable medium such as a memory stick, a hard-disk or other transportable or permanently-installed carrier can serve to transport and/or to store the executable parts of the computer program product so that these can be read from a processor unit of a device. A processor unit can comprise one or more microprocessors or their equivalents.

Particularly advantageous embodiments and features of the invention are given by the dependent claims, as revealed in the following description. Features of different claim categories may be combined as appropriate to give further embodiments not described herein.

According to a preferred method of an embodiment, in the case of receiving a dataset, this dataset is examined for information about authorization of certain users and marked accordingly when saving. This examination may be performed by an algorithm. Authorizations may be hierarchized, such as read only and read/write or read/comment or read/rate.

With the information about authorized users, also groups of users are meant or at least can preferably be designated. This has the advantage that data can be shared selectively, i.e. data can be shared with special users or user-groups. For example, research data of a group working in three hospitals can be shared in this group only and be invisible for other users. However, some results can be shared with a bigger community by rendering the authorizations accordingly, e.g. by marking it as accessible for all users.

It is preferred that the authorizations of certain users dictates which users are authorized to read and/or modify the data. The data can be marked that only special users may read them and additionally that a sub-group of these users can modify the data, wherein a preferred modification is a change of the data (e.g. a correction) and/or an addition, especially a comment, a rating, or additional data such as additional values of a measurement.

According to a preferred method of an embodiment, users can add a comment, which can be a text or a rating, such as thumbs up/thumbs down or with stars, to a dataset in the memory. This comment is then saved context-related to this dataset. Thus, a commented dataset comprises this comment. The advantage is especially, that users can rate an annotation (dataset) and the best dataset may be shown to a user prior the other datasets.

According to a preferred method of an embodiment, a time stamp and/or an information about the source is added for a dataset saved in the memory. Thus, annotations (datasets) can have a timestamp and can be linked to a specific doctor or institution.

According to a preferred method of an embodiment that allows a version control, changes to a dataset are tracked and preferably a history of changes to a dataset is sent to a user after a request. Thus, a device according to the invention is designed to track changes and continuously updates the latest developments and clinical best practices. This tracking of changes is well known, e.g. in office programs such as word.

According to a preferred method of an embodiment, information about authorized users of a dataset can be altered, preferably in that this information is received in the context of a dataset and the information about authorization of this dataset is adjusted according to this information. It is preferred that only the user developing this dataset can change authorization information, or at least authorized users may change these.

According to a preferred method of an embodiment, the content of a received dataset is examined, especially by an algorithm (e.g. an AI) and the dataset is saved according to the result of this examination. Here, the focus does not lie in the authorizations, but in the other content. It is preferred that a dataset is examined for information about a topic, especially a user, a source, a research program, medication, body region or a disease, and is saved context related to other datasets comprising the same topic (and the same genomic variation).

According to a preferred method of an embodiment, a user is able to link a user-identity with a genomic variation. The user-identity is the identity of the user regarding the communication. This can e.g. be the username or the IP (internet address). It is preferred that a notification is sent to this user when a new dataset is saved context related with this genomic variation.

According to a preferred method of an embodiment, a dataset is ranked according to comments of users, e.g. a user rating, and/or according to an evidence level.

According to a preferred method of an embodiment, a standardized input interface, especially an input mask, is used by all users. This has the advantage that it is ensured that participating institutions and doctors provide reliable and standardized datasets.

According to a preferred method of an embodiment, a genomic variation is identified with one or more of the following items:
  an unique gene ID,
  an unique transcript ID or specific genomic regions incl. reference genome,
  a variant definition according to Sequence Variant Nomenclature,
wherein preferably a user has the possibility to add
  an assignation of a evidence class describing the clinical actionability, and/or
  free text describing the variant and how it should be treated in a clinical context.

In addition, the system allows doctors to comment on and rate annotations added by other authorized persons.

In a preferred device according to an embodiment of the invention, components of the device are part of a data-network, wherein the data-network preferably comprises parts of the internet and/or a cloud-based computing system, wherein preferably the device according to the invention is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method of an embodiment may also include elements of "cloud computing". In the technical field of "cloud computing", an IT infrastructure is provided over a data-network, e.g. a storage space or processing power and/or application software. The communication between the user and the "cloud" is achieved by way of data interfaces and/or data transmission protocols.

In the context of "cloud computing", in a preferred embodiment of the method according to the invention, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of at least one embodiment of the system according to the invention, the abovementioned units (data interface, memory, computing unit) Are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

A preferred device of an embodiment comprises a login-interface designed to manage a login process of a user, preferably designed to verify credentials, to query user groups and/or to query user group access rights.

A preferred device of an embodiment comprises a query-interface designed to manage the output of datasets, preferably designed to identify genomic variants, verify gene names, verify variant names and/or to query variant data based on access rights, gene names, variant names and/or identifications of genomic variants.

A preferred device of an embodiment comprises an update-interface designed to manage a change of a dataset, preferably designed to verify treatment information and/or insert into a dataset a treatment and/or a comment, especially a rating.

One advantage of an embodiment of the invention is that annotations can be exchanged in a timely, reliable and standardized manner. By providing the possibility to comment and rate proposed annotations additional evidence is created. Furthermore, the proposed annotations are only shared with authorized clinics and partners. Users can define who should be able to see certain annotations, i.e. the system can be used to share annotations locally within institutions, between institutes or the greater community.

A physician can add variant annotation (data) to the inventive database an another physician can see the proposed annotation and comment on and rate the proposed annotation.

Although at least one embodiment of the invention is very advantageous in the fight against cancer, it is also advantageous regarding all diseases with genetic implications, such as e.g. cardio vascular diseases.

FIG. 1 shows a diagram of the process flow of a preferred method according to an embodiment of the invention for exchanging information regarding the clinical implications of genomic variations.

In step I, login-data L of a user U1 (see e.g. FIG. 2) are received.

In step II, the login-data L is evaluated, wherein in this example the login-data L are correct and the user U1 is logged in.

In step III, an encrypted data connection C to the user U1 is established.

In step IV, a dataset D is received in the context of a genomic variation and the received dataset D is saved in a memory 3 context-related with this genomic variation.

In step V, a user request R connected with a search query for a genomic variation is received and a set S of datasets D from the memory 3 is determined, wherein the datasets are context-related with this genomic variation and the set comprises these datasets that the user U1 is authorized to receive, and sent to the user U1.

For example, doctors in a first Hospital have gathered a lot of experience in the treatment of patients with NSCLC and EGFR-Inhibitors. They have observed that certain patients tend to develop a resistance mutation and need close monitoring. The doctors decide to add this important information to the common annotation resource. Doctors in a second Hospital do not have many NSLC patients and have not observed the behavior observed in the first Hospital before. They can now benefit from the knowledge gathered in the first Hospital and monitor patients matching the profile described in the according database entry.

In another example, Doctors in a first Hospital have treated a patient with a rare genetic variant that has only partially been described in literature. The doctors decide to test different treatment options in mouse models and eventually treat the patient with the most promising alternative. The doctors document their efforts in the common annotation database. Doctors in a second Hospital have a patient with the same genetic variant half a year later. The doctors can now benefit from the observations made by the doctors in the first Hospital and save valuable time in treating the patient.

Figure 2:
FIGS. 2A and 2B show the data flow of a preferred method according to an embodiment of the invention.
Figure 2A:
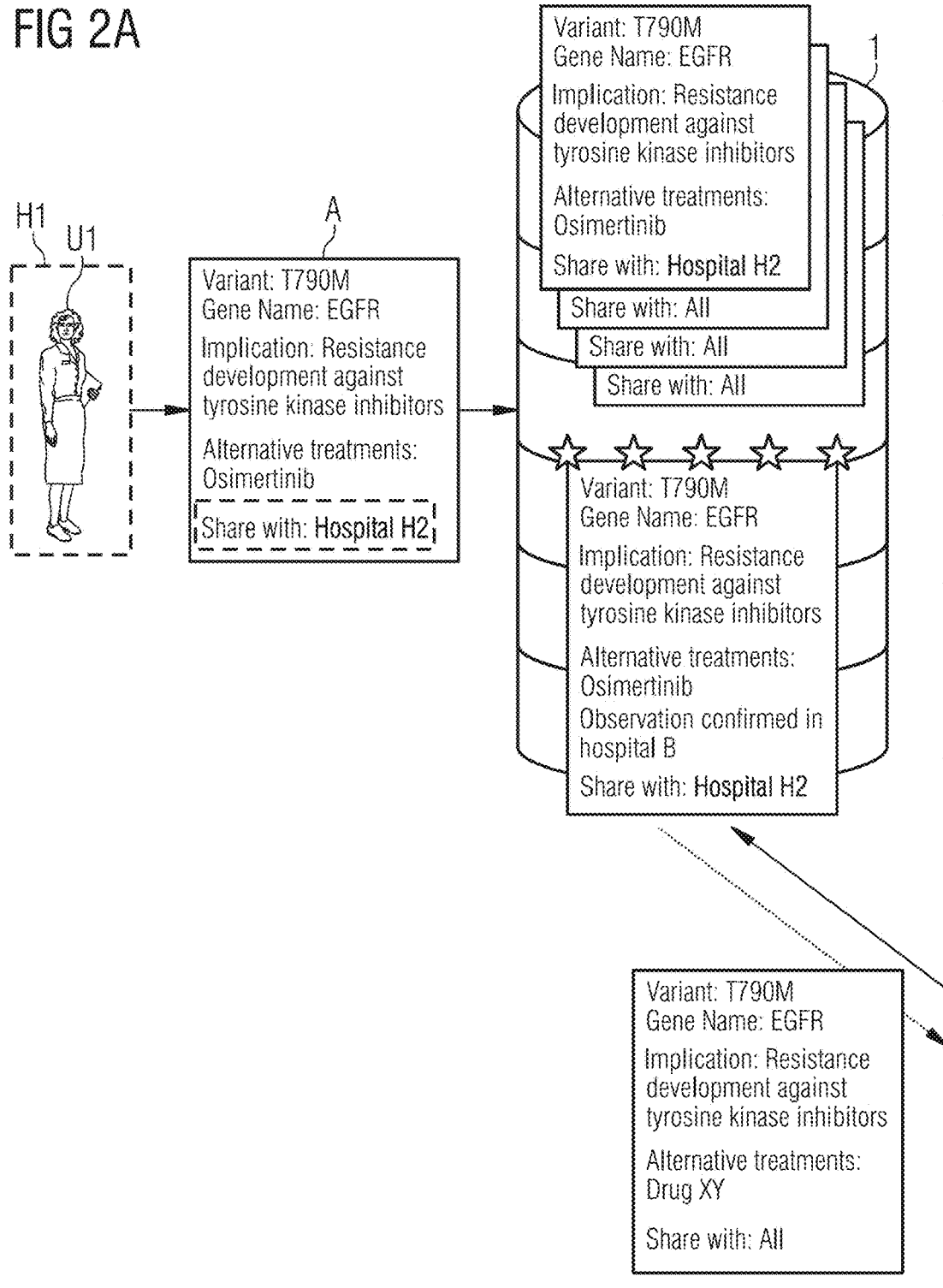
Figure 2B:
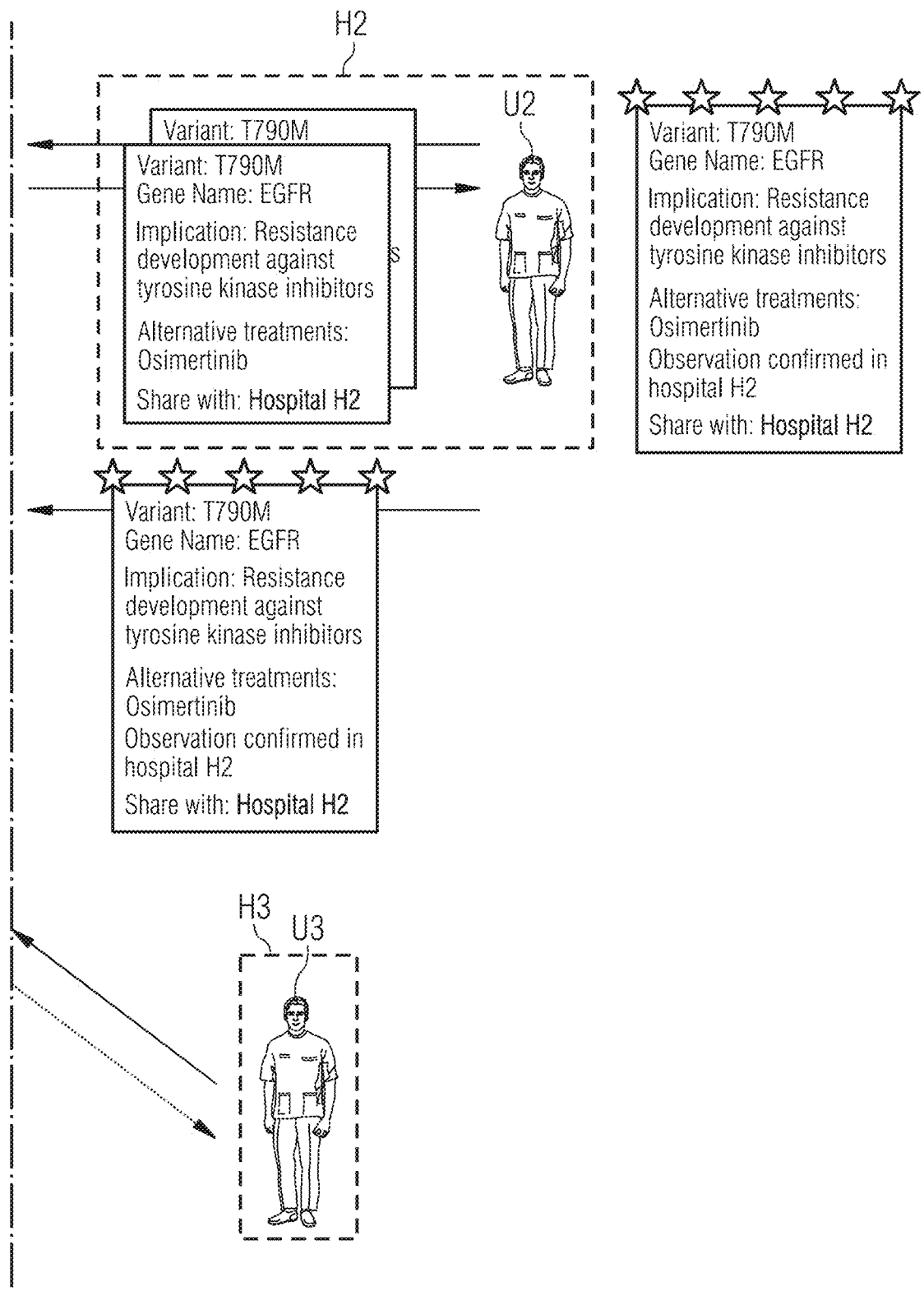

FIG. 2 shows the data flow of a preferred method according to an embodiment of the invention. A doctor (user U1) in a first hospital H1 has made an observation regarding the treatment of patients with EGFR T790M mutations, but isn't sure yet about the significance and only wants to share the observation with a certain second hospital H2. So, the doctor (user U1) creates a new entry (dataset D) for the genomic variant with "gene: EGFR" and "variant: T790M" with the implication: Resistance development against tyrosine inhibitors, and information about the alternative treatment Osimertinib. In addition, the dataset D comprises the information about authorization A that the dataset D should be shared with the second hospital H2, only.

The new entry is then sent to the database 1 and saved there.

A doctor (user U2) in the second Hospital H2 has a patient with T790M mutation in the EGFR gene and looks for alternative treatment options. The database 1 returns a list of entries that match gene: EGFR, variant: T790M with the new entry of the doctor in the first hospital H1. The doctor (user U2) in the second hospital H2 reviews and edits (ranks)

the new entry. The edited entry is then saved in the database 1 or updated in the database 1.

A doctor (user U3) in a third Hospital H3 has an interest in the EGFR gene and searches for "gene: EGFR". The database 1 returns a list of entries that match gene: EGFR, but the new entry for the T790M mutation is not available for the user U3, since he is not authorized.

Figure 3:
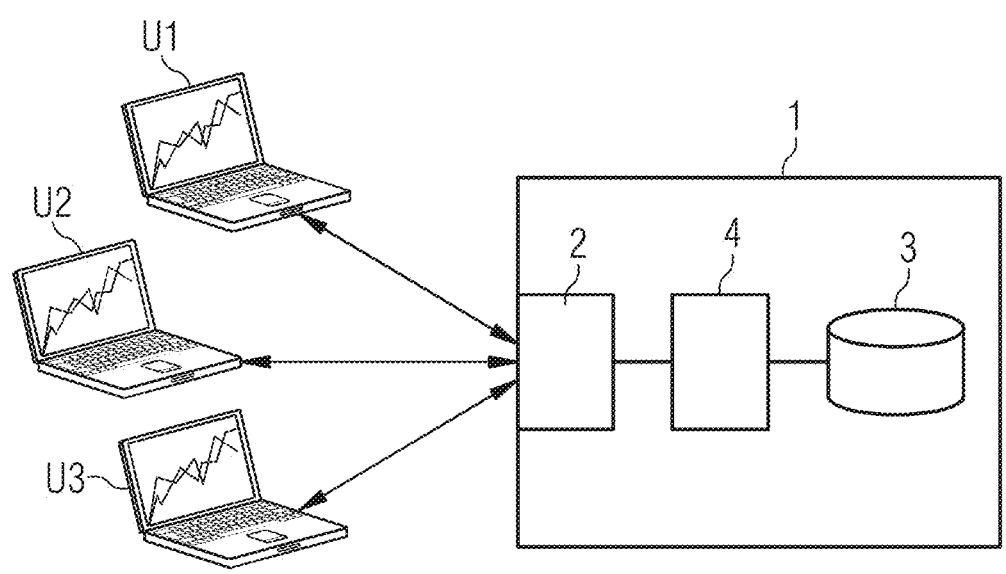
FIG. 3 shows a simplified device according to an embodiment of the invention.

FIG. 3 shows a simplified device 1 in form of a server 1 for a data network 5 according to an embodiment of the invention. The device 1 comprises a data-interface 2 designed for the exchange of data over the network 5, a memory 3 designed for saving data pertaining to clinical implications of genomic variations and a computing unit 4. The computing unit 4 is designed for evaluating login-data L of a user U1, U2, U3 (see e.g. FIG. 2) received over the data-interface 2, establishing an encrypted data connection C between the user U1, U2, U3 and the device 1 after a positive evaluation of the login data L, wherein in the case of receiving a dataset D in the context of a genomic variation, the received dataset D is saved in the memory 3 context-related with this genomic variation and in the case of a user request R connected with a search query for a genomic variation, a set S of datasets D from the memory 3 context-related with this genomic variation that the user U1, U2, U3 is authorized to receive is evaluated and send to the user U1, U2, U3.

FIG. 4 shows the inner architecture of a device 1 according to an embodiment of the invention (see e.g. FIG. 3). The device comprises three interfaces, a login-interface 6, a query interface 7 and a update-interface 8 that can be realized as software modules in the computing unit 4.

A user U1 sends login-data L comprising a login alias and a password to the login-interface 6. The login-interface 6 manages the login process and returns information about user groups and user statistics.

Then the user U1 enters a query input (a gene name and/or a (optional) variant name) to the query-interface 7. The query-interface 7 manages the query process and outputs variant details and variant treatment information to the user U1.

Then, the user U1 sends an update input (a comment) comprising a rating, information about favorites or new treatment information to an update-interface 8 that manages a change of a dataset D. The update-interface 8 returns a confirmation to the user U1.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for exchanging information regarding clinical implications of genomic variations, comprising:
    receiving login-data of a user;
    evaluating the login-data received;
    establishing an encrypted data connection to the user after the evaluating indicates a positive evaluation of the login-data;
    saving, upon receiving a dataset in a context of a genomic variation, the dataset received in a memory, context-related with the genomic variation; and
    evaluating, upon a user request being received and connected with a search query for the genomic variation, a set of datasets from the memory, the datasets being context-related with the genomic variation and the set including the datasets that the user is authorized to receive, and sending the set of datasets to the user.

2. The method of claim 1, wherein, upon receiving the dataset, the dataset is examined for information about authorization of certain users and is marked accordingly when saving.

3. The method of claim 1, wherein a comment to the dataset in the memory is receivable from the user, and wherein the comment is saved context-related to the dataset.

4. The method claim 1, wherein at least one of a time stamp and an information about a source is added for a dataset saved in the memory.

5. The method of claim 1, wherein changes to the dataset are tracked and a history of changes to the dataset is sent to the user after a request.

6. The method of claim 1, wherein information about authorization of users of the dataset is alterable, the information about authorization being received in the context of the dataset and the information about authorization of the dataset is adjusted according to the information.

7. The method of claim 1, wherein a content of the dataset received is examined and is saved context related to other datasets.

8. The method of claim 1, wherein a link of a user-identity with a genomic variation is receivable from a user.

9. The method of claim 1, wherein the dataset is ranked according to at least one of comments of users and an evidence level.

10. The method of claim 1, wherein a standardized input interface is used by all users.

11. The method of claim 1, wherein a genomic variation is identified with one or more of:
 a unique gene ID,
 a unique Transcript ID or specific genomic regions including a reference genome, and
 a variant definition according to Sequence Variant Nomenclature,
wherein, receivable from a user, are at least one of
 an assignation of a evidence class describing the clinical actionability, and
 free text describing the variant and how the variant should be treated in a clinical context.

12. A device for exchanging information regarding clinical implications of genomic variations, comprising:
 a data-interface designed for exchange of data over a network;
 a memory designed for saving data pertaining to clinical implications of genomic variations; and
 a computing unit designed for
  evaluating login-data of a user received via the data-interface;
  establishing an encrypted data connection between the user and the device after the evaluating indicates a positive evaluation of the login data;
  saving, upon receiving a dataset in a context of a genomic variation, the dataset received in the memory, context-related with the genomic variation; and
  evaluating, upon a user request being received and connected with a search query for the genomic variation, a set of datasets from the memory, the datasets being context-related with the genomic variation and the set including the datasets that the user is authorized to receive, and sending the set of datasets to the user.

13. The device of claim 12, further comprising at least one of
 a login-interface designed to manage a login process of the user,
 a query-interface designed to manage the output of datasets, and
 an update-interface designed to manage a change of a dataset.

14. A non-transitory computer program product storing a computer program, directly loadable into a server and including program elements for performing the method of claim 1 when the computer program is executed by the server.

15. A non-transitory computer-readable medium storing program elements, readable and executable by a computer unit, to perform the method of claim 1 when the program elements are executed by the computer unit.

16. The method of claim 2, wherein the authorizations of certain users dictates which users are authorized to at least one of read and modify the dataset.

17. The method of claim 16, wherein a comment to the dataset in the memory is addable by the users, and wherein the comment is saved context-related to the dataset.

18. The method of claim 2, wherein a comment to the dataset in the memory is addable by the users, and wherein the comment is saved context-related to the dataset.

19. The method claim 2, wherein at least one of a time stamp and an information about a source is added for a dataset saved in the memory.

20. The method of claim 7, wherein a content of the dataset received is examined by an algorithm and the dataset is saved according to the result of this examination.

21. The method of claim 7, wherein the dataset is examined for information about a topic and is saved context related to other datasets comprising the topic.

22. The method of claim 21, wherein the topic includes a user, a source, a research program, medication, body region or a disease.

23. The method of claim 8, wherein a notification is sent to the user when a new dataset is saved context related with the genomic variation.

24. The device of claim 12, further comprising at least one of
 a login-interface designed to manage a login process of the user, to at least one of verify credentials, query user groups and query user group access rights,
 a query-interface designed to manage an output of datasets, to at least one of identify genomic variants, verify gene names, verify variant names and query variant data based on at least one of access rights, gene names, variant names and identifications of genomic variants, and
 an update-interface designed to manage a change of a dataset, to at least one of verify treatment information and insert into at least one of a dataset a treatment and a comment.

* * * * *